United States Patent [19]

Forrest

[11] 4,438,068
[45] Mar. 20, 1984

[54] TEST-TUBE ASSEMBLY FOR IMMUNOASSAYS UTILIZING MAGNETICALLY ATTRACTABLE PARTICLES

[75] Inventor: Gordon C. Forrest, Ingatestone, England

[73] Assignee: Technicon Instruments Corporation, Tarrytown, N.Y.

[21] Appl. No.: 206,245

[22] Filed: Nov. 12, 1980

[30] Foreign Application Priority Data

Nov. 13, 1979 [GB] United Kingdom ............ 7939214

[51] Int. Cl.³ .......................................... G01N 33/54
[52] U.S. Cl. ...................................... 422/61; 422/68; 436/526; 436/806; 436/808; 436/824
[58] Field of Search .............. 436/526, 808, 806, 824; 422/68, 61

[56] References Cited

U.S. PATENT DOCUMENTS

| 4,141,687 | 2/1979 | Forrest | 436/808 X |
| 4,146,365 | 3/1979 | Kay | 436/526 X |
| 4,155,711 | 5/1979 | Zelagin | 436/808 X |
| 4,272,510 | 6/1981 | Smith | 436/526 X |

OTHER PUBLICATIONS

D. S. Ithakissios et al., Clin. Chem. 23(11), 2072–2079, (1977).

Primary Examiner—Sidney Marantz
Attorney, Agent, or Firm—S. P. Tedesco; C. J. Herron

[57] ABSTRACT

A test-tube assembly and method for carrying out immunoassays. The apparatus features two independent components, the first having a series of test-tubes fixed to a support and equidistantly dependent therefrom, and the second having a base including magnets permanently fixed therein, the two components being releasably couplable to hold the lower ends of the test-tubes adjacent the magnets in the base.

14 Claims, 7 Drawing Figures

TEST-TUBE ASSEMBLY FOR IMMUNOASSAYS UTILIZING MAGNETICALLY ATTRACTABLE PARTICLES

This invention relates to a test-tube assembly for use in a manual method of immunoassay, and to methods of assay using the assembly.

Many immunoassy procedures involve treating the liquid sample under assay (such a serum or urine) in a number of steps in sequence. For example, in certain competitive binding assays, the sample is incubated with a labelled competing reagent and a binding agent, the free fraction is then separated from the bound fraction and one or other fraction is then assayed for label. Such assays can be conducted wholly manually but they are time-consuming and require skilled personnel. Automatic analysis machines are available (such as the Technicon Autoanalyser) by which many immunoassays can be conducted on an automated basis, but such machines are necessarily complex and may not be warranted where the overall throughput of samples is relatively low.

In an attempt to speed up the manual assay procedure, it is known to carry out some of the steps in these assays on several samples simultaneously, i.e. to operate partially in a bath fashion. Thus, for example, a batch of test-tubes is placed in a rack, a portion of liquid sample is placed in each together with reagents, and the tubes are incubated. It has then usually been necessary, however, to carry out the further steps of the method, i.e. separation and label assay, on individual tubes by removing the tubes one by one from the batch, for respective treatment.

With the availability in recent times of magnetically attractable particles as reagents in immunoassays, proposals have been made for effecting a separation step in a bath manner. In one such proprosal (Nye et al, Clin. Chim. Acta, 69 (1976), 387–396), a rack of test-tubes is mounted over a large electromagnet and at the appropriate point in the assay, a magnetic field is applied to the tubes to cause magnetic particles suspended in liquid in the test-tubes to sediment. The supernatant from each tube is then aspirated for analysis.

In another proposal (Ithakissios and Kubiatowicz, Clin. Chem. 23/11 (1977), 2074–2079), there is described a magnetic separation rack consisting of a stainless steel housing with recesses in its base into which permanently magnetised bars can be inserted. The top of the rack contains 50 holes into which the assay tubes are placed, the tubes being held in the holes by spring-steel prongs. After forming in each tube a reaction mixture comprising the sample under away, a labelled substance and the magnetic particles, the particles are separated from the liquid by inserting the magnetic bars into the base of the rack (to cause the magnetic particles in each tube to sediment) and then inverting the rack so as collectively to decant the supernatant liquids whilst retaining the particles in each tube. The label remaining in the tubes (on the particles), or the label in the decanted supernatants, is then measured.

Whilst the arrangement described by Ithakissios and Kubiatowicz is useful, it has a number of serious disadvantages in practice. Principally, the necessity to remove and insert the magnetic bars is time-consuming and, in practice, such handling of the magnets reduces their magnetic strength. Further, the rack when loaded is relatively heavy for inversion and is fairly complex, and thus expensive, to manufacture.

We have now devised an improved test-tube assembly which is particularly designed for use with manual immunoassays utilising magnetic particles, and by which the disadvantages of prior proposals are reduced or overcome. Furthermore, in one highly preferred aspect of the invention, the assembly enables not only the separation step to be effected batchwise, but also the subsequent label assay step.

According to the invention, there is provided a two-part test-tube assembly for use in immunoassays utilising magnetically attractable particles, which comprises:

(a) a plurality of test-tubes mounted in a planar support member and fixedly held relative thereto, and the lower portions of the tubes projecting below the support member by a fixed distance; and (b) a substantially planar base member having magnet means permanently located therein;

the support member and the base member being releasably couplable together to form a unitary assembly in which the bottoms of the test-tubes are held adjacent the base member, the assembly being manually invertable (in use) whilst remaining unitary to decant liquids from the tubes whilst retaining magnetically attractable particles within said tubes under the influence of the magnet means.

The invention further provides a test-tube assembly for use in immunoassays utilising magnetically attractable particles, the assembly comprising:

(a) a support frame having a base and a pair of side members upstanding from opposed sides of the base, the base having permanently embedded therein one or more magnet means; and (b) a test-tube array comprising a substantially planar support member having a series of apertures therein, each aperture receiving a test-tube, the test-tubes being parallel to one another and substantially perpendicular to the said planar support, the lower portion of each test-tube depending below the planar support member a uniform distance, each test-tube being firmly held against movement within its respective aperture; and (c) means for releasably mechanically coupling the planar support to the upstanding side members to form an integral unit assembly of said array and the said frame, in which assembly the lower end of each tube is located adjacent the magnet means in the base of the frame, the assembly being manually invertable without movement of the test-tubes relative to the planar support or the said base.

The invention also includes a manual method of immunoassay for analytes in liquid samples, which comprises:

(i) forming in each of a series of test-tubes a reaction mixture comprising a respective sample to be assayed, a labelled substance and a binding agent immobilised on magnetically attractable particles suspended in the mixture, the test-tubes being in an array comprising a substantially planar support member having a series of apertures therein, each aperture receiving a respective test-tube with the lower portion of each tube depending below the planar support member, each tube being firmly held within its respective aperture;

(ii) releasably coupling the array to a base member having permanently embedded therein one or more magnet means, whereby the lower portion of each tube is located in the assembly adjacent the magnet means in said base of the frame so that the suspended particles in each test-tube are sedimented under the influence of the magnet means;

(iii) manually inverting the assembly to decant the liquid from each test-tube whilst retaining the said particles in each tube under the continuing influence of the magnet means; and (iv) measuring the label in the particles or in the decanted liquid from each tube to assay the respective analytes.

The invention further includes a method of manual immunoassay for analytes in liquid samples, wherein there is used a two part test-tube assembly which comprises:

(a) a plurality of test-tubes mounted in a planar support member and fixedly held relative thereto, and the lower portions of the tubes projecting below the support member by a fixed distance; and (b) a substantially planar base member having magnet means permanently located therein;

the support member and the base member being releasably couplable together to form a unitary assembly in which the bottoms of the test-tubes are held adjacent the base member.

In the test-tube assemblies of the invention, the magnet(s) in the base are permanently located. Thus, they remain fixed in position in the base throughout the use of the base in an assay. We prefer to use as the base a plastics moulding in which the magnet(s) is (are) embedded, but other arrangements in which the or each magnet is fixed in the base can of course be used.

The number and size of the magnets themselves will depend on the size of the test-tube assembly, i.e. on the number and spacing of the test-tubes. One or more bar magnets may be used, suitably with a pole immediately below a test-tube so as to subject the end of the tube to a strong field. Alternatively, there may be a single magnet for each tube, such as a rare earth magnet, each such magnet being located directly under its respective tube in the assembly.

The test-tubes are mounted in a planar support member so that preferably the open ends thereof project at least slightly, above the support. The lower portions depend below the support by a fixed distance determined by the dimensions of the assembly, so that the bottoms of the tubes in the assembly will lie close to the base member. The test-tubes are firmly held in the support member so that no casual movement thereof relative to the support can occur. In one preferred arrangement, the support and test-tubes can be formed as a one-piece moulding. In other arrangements, test-tubes can be inserted through pre-formed orifices in a support member, the orifices being sized to provide a tight friction fit. For such purposes, plastics or strong cardboard supports may be used, for example, or light wooden panels. It is also possible, although much less preferably, to provide clips or other devices which can be attached to the individual tubes to hold them firmly located relative to the support. Such an arrangement is not recommended, however, because it is an unnecessary complication and a possible source of error in that a tube may inadvertently become loose and be dislodged.

For general purposes, the tubes must be firmly located in the support member for two principal reasons, firstly to ensure that during inversion of the assembly they do not drop out of the support, and secondly to ensure that in the assembly the bottoms of the tubes lie in the desired positions relative to the magnets in the base. There is a third important reason why, in a highly preferred embodiment of the invention, the tubes must be firmly located in the support, to be described hereinafter.

The support member (with test-tubes) is releasable couplable to the base member, i.e. it can be coupled thereto and then released therefrom. In the coupled state, the lower ends of the test-tubes are held positioned adjacent the, or the respective, magnets in the base. There are many ways in which the support and base can be arranged in order to achieve this releasable coupling and particular orientation in the coupled state. For example, one or both components may be provided with side walls in which are formed a pair of grooves for slidably receiving the other component. Instead of grooves, co-operating projections and recesses may be provided on the two components. In another arrangement, coupling is achieved by providing a pair of inwardly inclined flanges on side walls on the base, the test-tube array then being slidably received between the flanges, walls and base.

A less preferred arrangement consists in providing separate clip or other joining means which can be applied to the base and test-tube array to hold them together. For example, if the base and array have surfaces which are contiguous, a spring clip or the like can be applied to temporarily hold the components together. This type of coupling, whilst possible, is not recommended in that it involves at least one separate coupling member and it is generally unnecessary. We very much prefer to so shape the base and the test-tube support that they can be coupled firmly together without the use of a separate coupling member. Apart from such arrangements described, one or both of the base and support may have clips or other devices integrally therewith to engage and co-operate directly with counterpart devices on the other component when the two components are brought into assembly.

The assemblies of the invention, particularly when made of plastics or strong cardboard, are light and very easily handled (e.g. with one hand). This is an important feature of the invention since some of the prior art proposals are relatively heavy and cumbersome.

Very recently, there have become available multi-head counters whereby the contents of a plurality of tubes can be simultaneously and individually counted for a radioactive label. In all prior proposals for manual assays, it has been necessary after the separation step, to remove each tube from the test-tube rack and place it in a counter. According to a highly preferred feature of the present invention, not only is the separation step effected batchwise, but so also is the counting. This is achieved by using an assembly of the invention in which the arrangement of the test-tubes exactly matches the arrangement of the orifices in a multi-head counter (there being no more test-tubes in the array than there are orifices in the counter). After the separation step, the test-tube array is released from the assembly as a unit, and offered to the counter, the lower portion of each tube below the support being simultaneously received in a counting orifice in the counter. Counting is then effected. It will be appreciated that, for this purpose, the test-tube support should not have any side walls or other projections which might interfere with the insertion of the tubes into the counter.

It is a highly advantageous step in a manual radioassay to be able to count a series of tubes without having to handle the tubes individually. This aspect of the invention is not exclusive to radioassays: multi-head counters for other labels, e.g. fluorescent labels, may also be utilized. Whilst, in theory, there is little or no restriction on the possible arrangement and number of counting orifices which can be provided in a multi-head counter, such counters as are presently commercially available have either 10 or 16 orifices, arranged in two parallel lines with, respectively, 5 or 8 orifices in each line. Where such counters are to be used, therefore, the test-tubes will be arranged in the support in two parallel lines matching the orifice arrangement.

In the method of assay of the present invention, a reaction mixture is formed in each of a series of test-tubes. Usually, the tubes will already be in position in a support member of the two part assembly of the invention, but the support member will not at this stage be coupled to the magnetic base. The reaction mixture will include a sample of the liquid containing the analyte under assay and one or more reagents depending on the particular assay being performed. One reagent will comprise finely divided magnetic particles bearing a reactant or binding agent, and another reagent will comprise a label such as a radio-active atom. In one example of assay, a competitive binding reaction occurs between the analyte and the particles (on the one hand) and between the labelled substance and the particles (on the other hand), and by measuring the amount of label becoming bound to the particles, a measure of the amount of analyte in the original sample can be obtained. It will be appreciated that this is merely one example of the many assay methods known in the art utilising magnetic particles. Magnetic particles for use in immunoassays are known in the art and are described, for example, in our U.S. Pat. No. 4,141,687 to which reference may be made for further details.

Having formed the reaction mixtures in the test-tubes, the mixtures may be incubated as necessary for a sufficient period for reaction to occur. During this time, the tubes may if necessary be shaken to maintain the magnetic particles in suspension. There then follows the separation step. The test-tubes, firmly located in their planar support, are offered to the magnetic base, the support being releasably coupled thereto to form an assembly of the invention. The lower portions of the test-tubes are thus held in the magnetic field of the magnets in the base, and the magnetic particles quickly sediment to the bottom of each tube. The assembly is then inverted to decant the supernatant liquid from each tube whilst retaining the magnetic particles in each tube. If desired, the liquid from each tube can be collected and stored for assay, but more usually it is passed to waste. The assembly is then re-inverted (i.e. brought back to the right way up) and the label-bearing magnetic particles in each tube are measured for label, after washing as desired. If the test-tube arrangement in the support matches a multi-head counter, the support is simply uncoupled from the base and offered to the counter. Otherwise, the tubes are removed individually from the support and counted.

Whilst the test-tube assemblies of the invention are intended principally for use in the method of the invention as described above, they may also be used in other slightly different methods. Thus, for example, they may be used in assays where, instead of inverting the assembly to decant the liquid, the liquid is aspirated from each tube whilst the magnetic particles are held sedimented in the assembly. Alternatively, instead of using magnetic particles, a reagent coating may be provided on the inner wall of each test-tube, the coating becoming bound to a portion of the label from the reaction mixture. Inversion of the assembly removes the liquid, leaving the coating intact on the tubes. The label content of the tubes may then be measured. This procedure is particularly useful when the test-tube arrangement matches the multi-head counter.

In another procedure using an optical label (such as a fluorescent label), no separation step need be used. The test-tube walls are optically transparent and after sedimentation of the magnetic particles, the label in the supernatant is assayed by measurement through the walls of each test-tube at a level above the sedimented magnetic particles.

BRIEF DESCRIPTION OF THE DRAWINGS

In order that the invention may be more fully understood, embodiments thereof will now be described, by way of example only, with reference to the accompanying drawings, in which:

Referring to FIGS. 1 to 4 (in which like numerals indicate like parts), the test-tube support 1 is a one piece plastics moulding in the form of a shallow tray with sides 2 upstanding from a base 3 and test-tubes 4 depending from the base 3 below the tray. The open end 5 of each tube is flush with base 3. At each end of support 1 is a handle or lip portion 6 to assist in handling the support and also to engage in the magnetic base (FIG. 2) for releasable coupling therewith.

Figure 1:
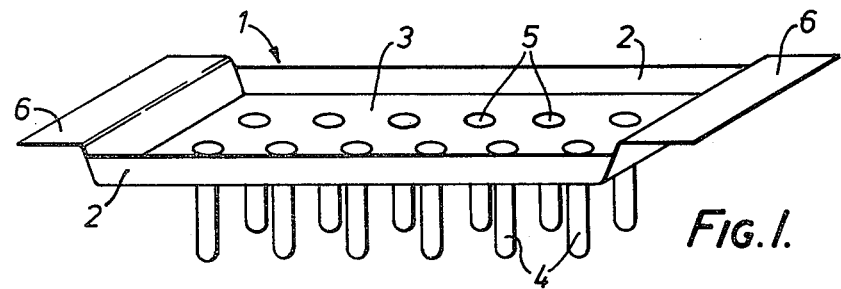
FIG. 1 is a perspective view of a support with test-tubes.
Figure 2:
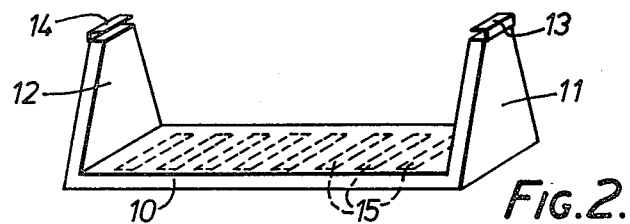
FIG. 2 is a perspective view of a magnetic base for receiving the support.
Figure 3:
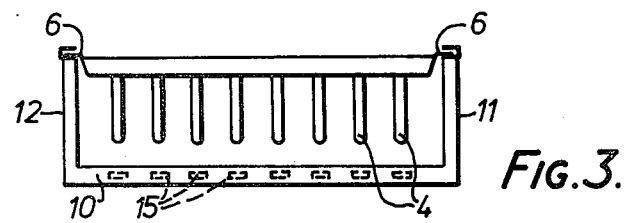
FIG. 3 is a front elevation of the assembly of support and base of FIGS. 1 and 2.

The magnetic base of FIG. 2 comprises a base member 10 with upstanding end walls 11,12, each having a longitudinal groove 13,14 at its upper end to receive the respective portions 6 of the test-tube support of FIG. 1 (see FIG. 3). Base member 10 has a series of bar magnets 15 embedded therein, the arrangement being such that in the assembly, each bar magnet lies immediately below a pair of test-tubes 4. As FIG. 3 shows, the lip portins 6 of the test-tube support 1 are received in grooves 13,14 of the base member walls, to releasably couple the two components together. Instead of a lip and groove arrangement, other coupling means can equally be used, e.g. clips or another form of mating engagement of the two components.

Figure 4:
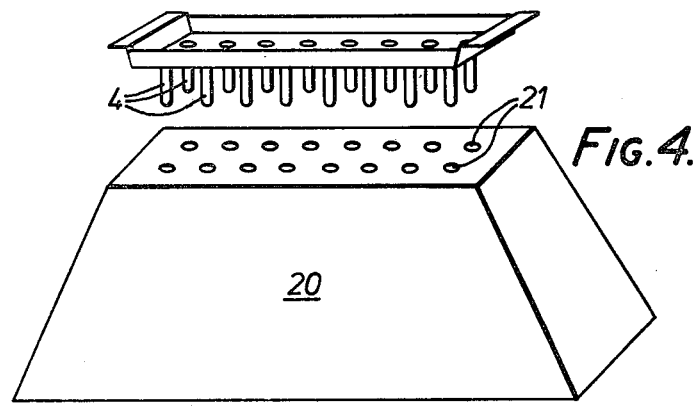
FIG. 4 illustrates use of a multi-head counter with the test-tubes of FIG. 1.

FIG. 4 illustrates diagrammatically a multi-head counter module 20, with sixteen counting orifices 21. An assembly of FIG. 1 is shown above the counter, the orifices 21 being arranged to receive the assembly 1 of tubes as the assembly is lowered towards the counter.

Figure 5:
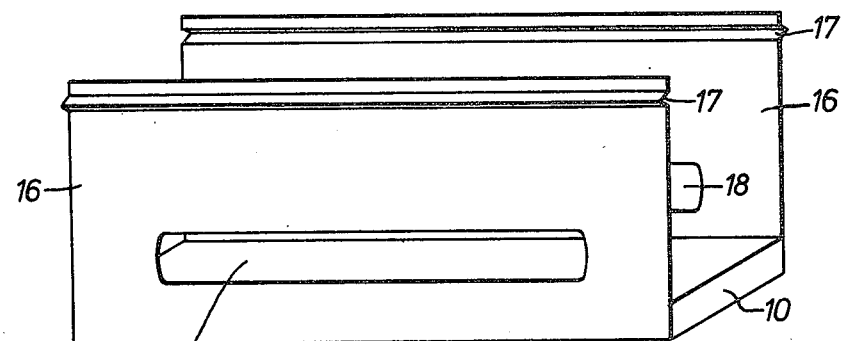
FIG. 5 is a perspective view of a second embodiment of magnetic base.
Figure 6:
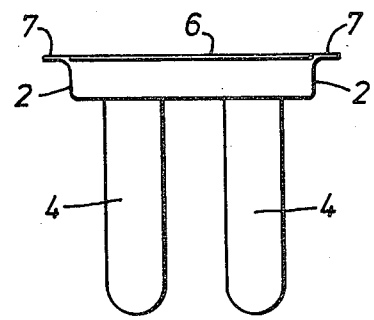
FIG. 6 is an end view of a test-tube support for use with the base of FIG. 5.

The magnetic base unit of FIG. 5 is for use with the test-tube support of FIG. 6. The unit of FIG. 5 comprises a base 10 having a series of permanent magnets (not shown) embedded therein (as in FIG. 2). Unlike FIG. 2, however, the unit of FIG. 5 has a pair of upstanding side walls 16 (but no end walls). Near the top of each wall 16 is provided a longitudinal channel 17 parallel to the base 10 and extending the full length of each wall. Each wall also has a longitudinal cut-out portion 18 to enable the user to see the test-tubes when the unit is in use with test-tube arrangement of FIG. 6.

The grooves 17 are designed to receive the flanges 7 of the unit of FIG. 6 (in which like numerals indicate like parts to FIG. 1), as the unit is slid longitudinally into the base unit. The length of the test-tube support is the same as, or close to, that of the base unit to form a compact combination for inversion. The magnets in base 10 are so placed that, preferably, each pair of tubes 4 in the assembly lies directly over a magnet.

Figure 7:
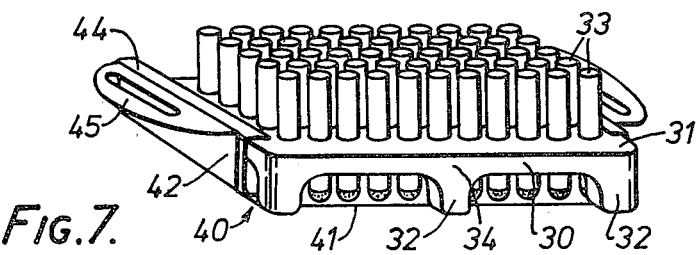
FIG. 7 is a perspective view of a third embodiment of assembly according to the invention.

FIG. 7 shows an assembly of the invention in which the test-tube support 30 is being slid into a magnetic base member 40. The support 30 is a plastics moulding having a planar region 31 and depending short legs 32. Holes are formed in the planar region 31, in which holes test-tubes 33 are received in a tight friction fit. The base member 40 has individual magnets (not shown) in its planar base portion 41, one magnet for each test-tube. A pair of upstanding side-walls 42 (only one is visible in the drawing) each have both an inner flange 44 and an outer flange 45 in the form of a handle. The assembly is formed by sliding the unit 30 into the base member 40, as shown, between the flanges 44, the side walls 42 and the planar base 41. As drawn, the unit 30 has not quite been slid to its final position, in which its front face 34 is flush with the ends of side walls 42.

In the embodiments illustrated in FIGS. 1 to 6, the support and test-tubes therein are shown as an assembled unit. As stated previously, such unit may be a single integral plastics moulding, or it may be formed by inserting test-tubes in a generally planar apertured support member. In the latter case it can be a problem in practice, when inserting the test-tubes in the support, to ensure that all the test-tubes project an appropriate distance below the support so that, when the support is coupled to the magnetic base, the bottoms of the tubes lie adjacent the magnets. According to a preferred feature of the present invention, this problem can be overcome by first coupling the apertured test-tube support member (without test-tubes in it) to the magnetic base member. Then, individual test-tubes are inserted in the apertures in the support member and pushed home to a position in which the bottom of each tube is located just above, or on, the magnetic base. After loading the test-tubes in the support in this fashion, the support may be uncoupled from the magnetic base member for performing the assay.

Another advantage of this procedure is that, as each tube is fitted into its respective aperture in the support member, it can be accurately located with respect to any particular magnet in the magnetic base.

The use of the magnetic base member as a "template" for loading the test-tubes into the apertured test-tube support member is particularly advantageous for "one-use" kits, i.e. kits in which the components are discarded to waste when an assay is completed. For this purpose, the test-tube support member may be of stiff cardboard (or similar material) or of plastics, the apertures therein being sized to receive the test-tubes in a tight friction fit. Separate means for holding the tubes with respect to the support may be provided but this is generally unnecessary and not preferred. The invention thus includes a kit for making a test-tube assembly for use in immunoassays utilising magnetically attractable particles, the kit comprising:

(a) a plurality of substantially identical test-tubes;
(b) a generally planar apertured support member, each aperture being sized to receive a test-tube in tight friction fit therein;
(c) a substantially planar base member having magnet means permanently located therein;
and wherein means are provided for releasably coupling the apertured support member to the magnetic base member in a substantially parallel and overlying configuration; the test-tubes being insertable in the apertured support with their bottom ends lying adjacent the magnetic base member in the assembly; the assembly being manually invertable (in use) whilst remaining unitary to decant liquids from the tubes whilst retaining magnetically attractable particles within the tubes under the influence of the magnet means.

I claim:

1. A two-part test-tube assembly for use in immunoassays utilising magnetically attractable particles, which comprises:
   (a) a plurality of test-tubes mounted in a planar support member and fixedly held relative thereto, and the lower portions of the tubes projecting below the support member by a fixed distance; and
   (b) a substantially planar base member having magnet means permanently located therein;
the support member and the base member being releasably couplable together to form a unitary assembly in which the bottoms of the test-tubes are held adjacent the base member, the assembly being manually invertable (in use) whilst remaining unitary to decant liquids from the tubes whilst retaining magnetically attractable particles within said tubes under the influence of the magnet means.

2. An assembly according to claim 1, in which the test-tubes and the planar support member in which they are located are a single one-piece plastics moulding.

3. An assembly according to claim 1, wherein the planar support member is a plastics moulding having a series of apertures therein, and wherein a test-tube is received in each aperture in a tight friction fit therein.

4. An assembly according to claim 1, in which the arrangement of test-tubes in the support member matches the arrangement of orifices in a multi-head counter, whereby the lower portion of the tubes can be simultaneously received in the said orifices as the support member is offered up to the counter.

5. An assembly according to claim 1, wherein the base comprises a generally planar member comprising a plurality of permanent bar magnets embedded in a synthetic polymeric matrix.

6. An assembly according to claim 5, in which the base comprises a plurality of magnets, one magnet for each test-tube.

7. A test-tube assembly for use in immunoassays utilising magnetically attractable particles, the assembly comprising:
   (a) a support frame having a base and a pair of side members upstanding from opposed sides of the base, the base having permanently embedded therein one or more magnet means;
   (b) a test-tube array comprising a substantially planar support member having a series of apertures therein, each aperture receiving a test-tube, the test-tubes being parallel to one another and substantially perpendicular to the said planar support, the lower portion of each test-tube depending below the planar support member a uniform distance, each test-tube being firmly held against movement within its respective aperture; and (c) means for releasably mechanically coupling the planar support to the upstanding side members to form an integral unit assembly of said array and the said frame, in which assembly the lower end of each tube is located adjacent the magnet means in the base of the frame, the assembly being manually invertable without movement of the test-tubes relative to the planar support or the said base.

8. An assembly according to claim 7, wherein the said coupling means comprises a pair of grooves, one formed in each of said upstanding support member, the grooves being parallel to the base member and arranged to slidably receive a pair of opposed side edges of the planar support member.

9. An assembly according to claim 7, wherein the coupling means comprises co-operating projections and recesses formed on said support frame and on said test-tube array.

10. An assembly according to claim 7, wherein said coupling means comprises a pair of inwardly inclined flanges from said saide members, said test-tube array being slidably receivable in said support frame between said flanges and said base.

11. A test-tube assembly for use in immunoassays utilising magnetically attractable particles, which comprises:

(a) a generally planar support member having a series of apertures therein, each aperture receiving in tight friction fit a test-tube, the lower portions of the tubes projecting below the support member by a uniform fixed distance; and (b) a generally planar base member having magnet means permanently located therein;

the support member and the base member being releasably couplable together to form a unitary assembly in which the bottoms of the tubes are held adjacent the base member, the assembly being manually invertable (in use) whilst remaining unitary to decant liquids from the tubes whilst retaining magnetically attractable particles within the tubes under the influence of the magnet means.

12. An assembly according to claim 11, wherein component (a) is formed by coupling the apertured support member to the base member, and inserting to each aperture of the support member a test-tube, to project below the said support member so that the bottom of each tube lies adjacent the base member; the tubes being received in the apertures in a tight friction fit.

13. An assembly according to claim 11, wherein the support member is cardboard or plastics material.

14. A kit for making a test-tube assembly for use in immunoassays utilising magnetically attractable particles, the kit comprising:

(a) a plurality of substantially identical test-tubes;

(b) a generally planar apertured support member, each aperture being sized to receive a test-tube in tight friction fit therein;

(c) a substantially planar base member having magnet means permanently located therein;

and wherein means are provided for releasably coupling the apertured support member to the magnetic base member in a substantially parallel and overlying configuration; the test-tubes being insertable in the apertured support with their bottom ends lying adjacent the magnetic base member in the assembly; the assembly being manually invertable (in use) whilst remaining unitary to decant liquids from the tubes whilst retaining magnetically attractable particles within the tubes under the influence of the magnet means.

* * * * *